US00PP37074P2

(12) United States Plant Patent
Hung et al.

(10) Patent No.: US PP37,074 P2
(45) Date of Patent: Oct. 28, 2025

(54) ***PHILODENDRON* PLANT NAMED 'HUTAPD75'**

(50) Latin Name: *Philodendron erubescens*
Varietal Denomination: HUTAPD75

(71) Applicant: Huta Green Company Limited, Hanoi (VN)

(72) Inventors: Pham Ngoc Hung, Hanoi (VN); Le Tuan Anh, Hanoi (VN)

(73) Assignee: Huta Green Company Limited, Hanoi (VN)

( * ) Notice: Subject to any disclaimer, the term of this patent is extended or adjusted under 35 U.S.C. 154(b) by 0 days.

(21) Appl. No.: 18/831,559

(22) Filed: Apr. 17, 2025

(51) Int. Cl.
*A01H 5/12* (2018.01)
*A01H 6/10* (2018.01)

(52) U.S. Cl.
USPC ..... Plt./381

(58) Field of Classification Search
USPC ..... Plt./381
CPC ..... A01H 5/12; A01H 5/00; A01H 6/10
See application file for complete search history.

(56) References Cited

U.S. PATENT DOCUMENTS

PP36,203 P2 * 10/2024 Ward ..... Plt./381

* cited by examiner

*Primary Examiner* — June Hwu
(74) *Attorney, Agent, or Firm* — Samuel R. McCoy, Jr.

(57) ABSTRACT

'HUTAPD75' is a distinctive *Philodendron* plant which is characterized by uniquely variegated laminas with a green base coloration, light yellow to golden yellow flecking, and irregular blotches of varying size and color, from near-white to yellow, as well as green petioles and petiole wings with a combination of near-white and light yellow irregular longitudinal stripes, and the stability of all characteristics from generation to generation.

3 Drawing Sheets

Latin name of the genus and species: The Latin name of the genus and species of the novel variety disclosed herein is *Philodendron erubescens*.

Variety denomination: The inventive variety of *Philodendron* disclosed herein has been given the variety denomination 'HUTAPD75'.

BACKGROUND OF THE INVENTION

Parentage: 'HUTAPD75' is a spontaneous whole-plant mutation which was discovered in 2022 at a commercial greenhouse facility in Hanoi, Vietnam, growing amongst a cultivated population of *Philodendron erubescens* 'White Wizard' plants (not patented). The mutation was first noted for its tricolored foliage variegation, relative to the bicolored variegation of 'White Wizard'. Meristematic tissue was harvested from said mutation and in vitro micropropagation was performed, resulting in a plurality of tissue cultured plantlets. Each of these plantlets was subsequently grown in a greenhouse from 2022 through 2023 to confirm the stability and relative uniformity of the unique foliage colorations that were first observed on the whole plant mutation in 2022. In 2023, one of the resulting plants was determined to have a stable, tricolored variegation pattern and was selected for further propagation. This new plant was given the name 'HUTAPD75'.

Asexual Reproduction: Asexual reproduction of the new cultivar 'HUTAPD75', by way of meristematic tissue culture micropropagation, was first initiated in 2024 in Hanoi, Vietnam. Through six subsequent generations, the unique features of this cultivar have proven to be stable and true to type.

SUMMARY OF THE INVENTION

The cultivar 'HUTAPD75' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HUTAPD75'. These characteristics in combination distinguish 'HUTAPD75' as a new and distinct *Philodendron* cultivar:

1. *Philodendron* 'HUTAPD75' exhibits uniquely variegated laminas with a green base coloration, light yellow to golden yellow flecking, and irregular blotches of varying size and color, from near-white to yellow; and
2. *Philodendron* 'HUTAPD75' exhibits green petioles and petiole wings with a combination of near-white and light-yellow irregular longitudinal stripes, and the stability of all characteristics from generation to generation.

BOTANICAL DESCRIPTION OF THE PLANT

Figure 1:
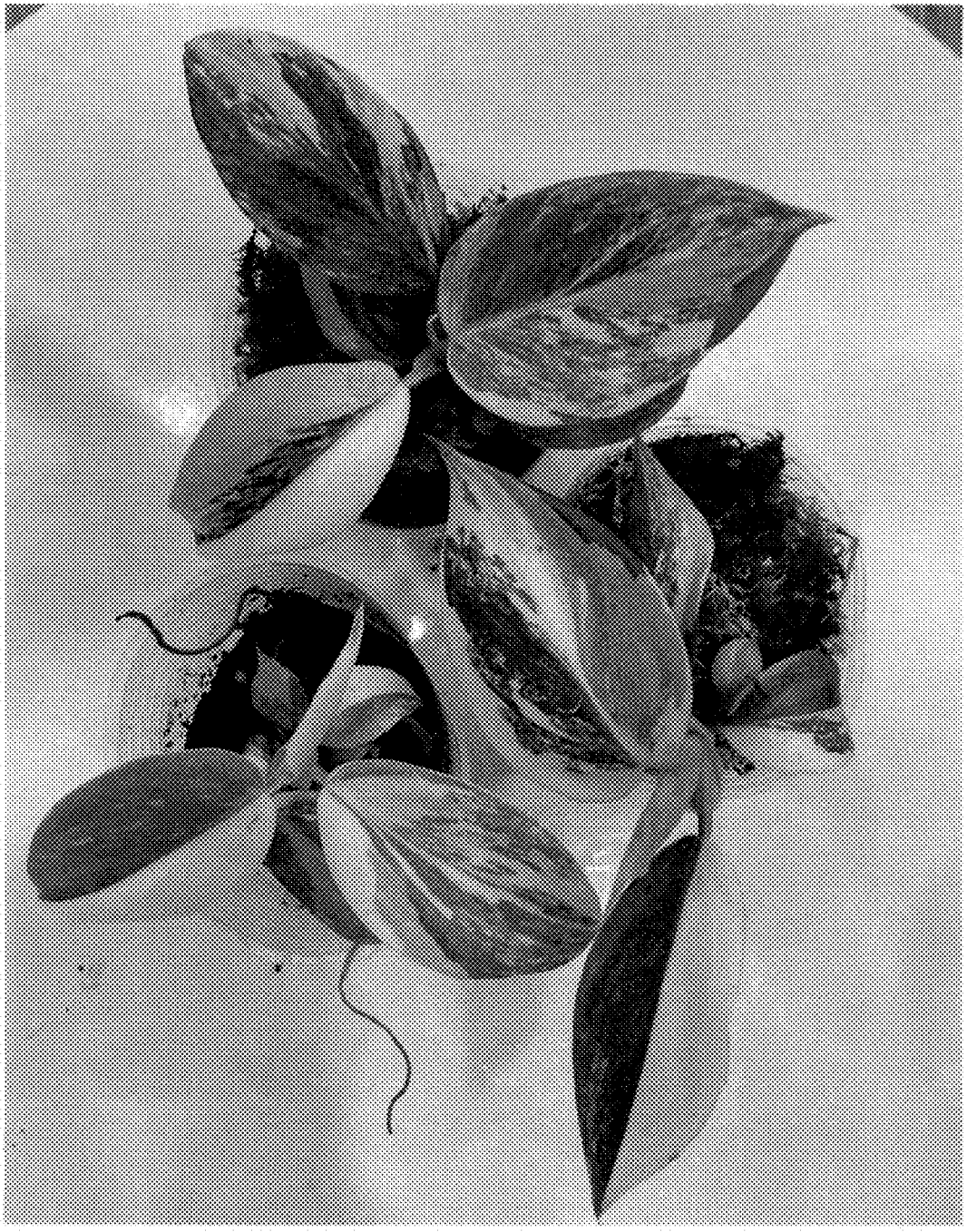
FIG. 1 illustrates, as nearly true as it is reasonably possible to make the same in color photographs of this type, three exemplary plants of 'HUTAPD75' grown in a commercial greenhouse in Hanoi, Vietnam. These plants are approximately 6 months old, in a 10 cm container.
Figure 2:
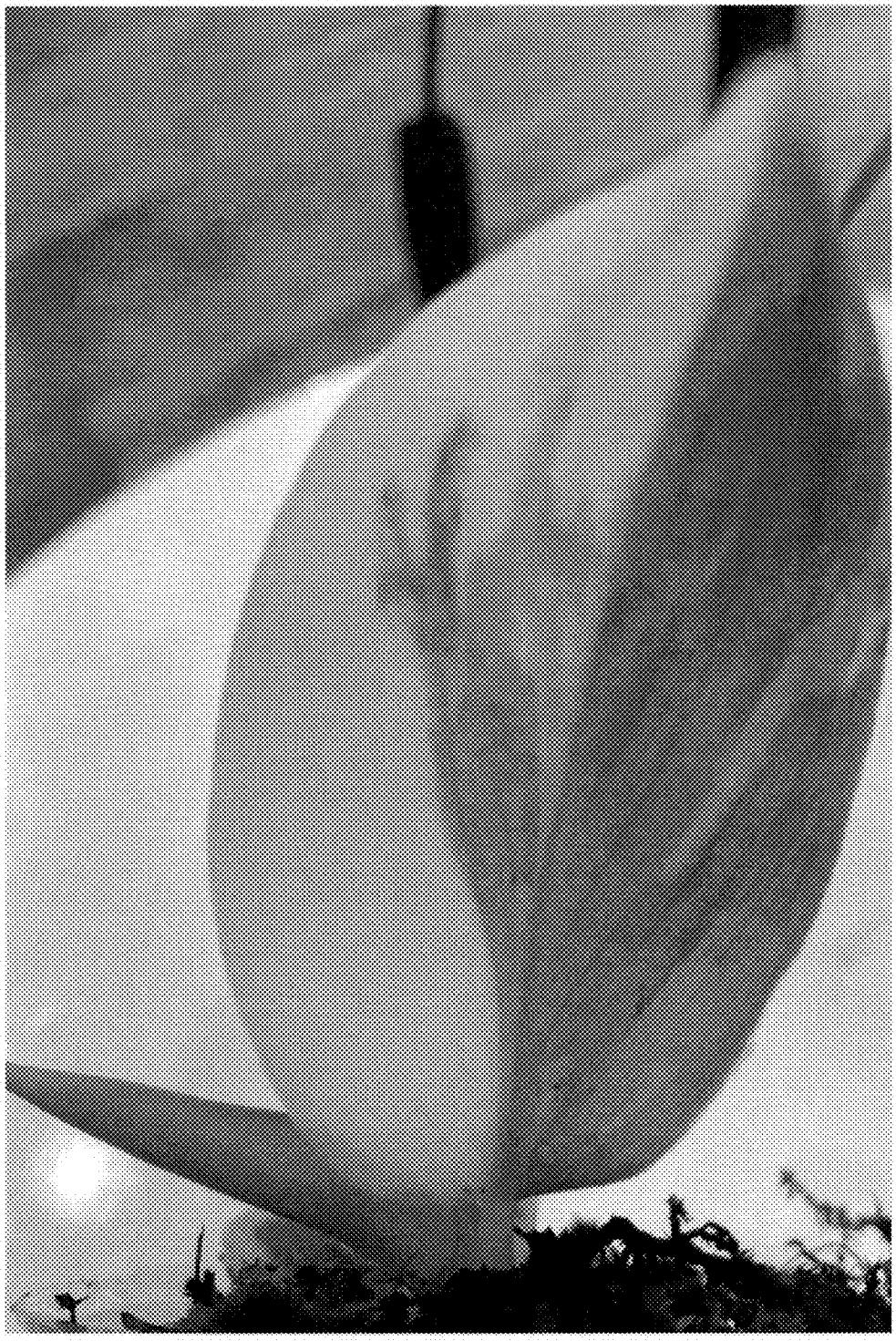
FIG. 2 illustrates, as nearly true as it is reasonably possible to make the same in color photographs of this type, the mature foliage's abaxial surface of 'HUTAPD75'.
Figure 3:
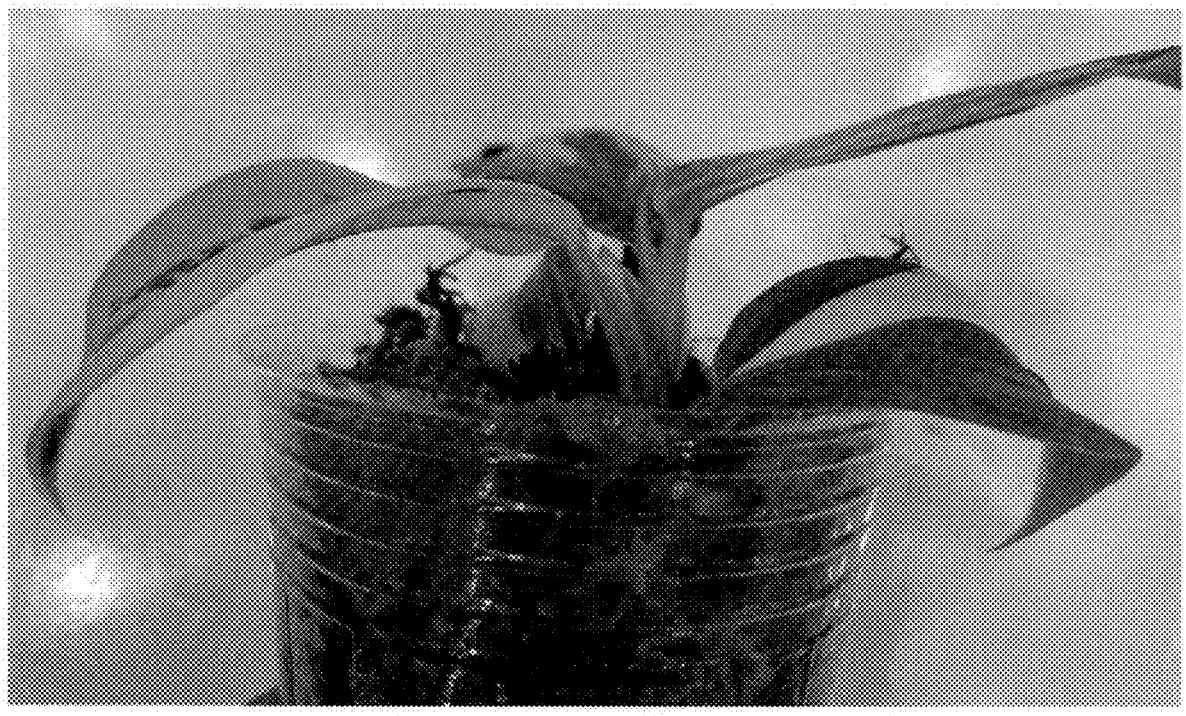
FIG. 3 illustrates, as nearly as it is reasonably possible to make the same in color photographs of this type, a lateral view of 'HUTAPD75'.

The following observations and measurements, made in February of 2025, describe averages from a 6-month-old 'HUTAHM05' plant grown in a 10 cm nursery container at commercial greenhouse in Hanoi, Vietnam. Plants were produced using conventional greenhouse production protocols for *Philodendron* species which consisted of overhead irrigation twice a week, weekly applications of a liquid 20-20-20 fertilizer at an electroconductivity of 0.8, and anti-bacteria oxalinic acid at a rate of 375 parts-per-million and Imidacloprid insecticide at a rate of 100 parts-per-million applied every two weeks. Plants were grown under shade (ranging from 5,000 to 20,000 lux) with ambient temperatures ranging from 20 to 35 degrees Celsius and humidity levels ranging from 60 to 95 percent.

Those skilled in the art will appreciate that certain characteristics will vary with older or, conversely, with younger plants. 'HUTAPD75' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'HUTAPD75' and a comparison with the parent plant and most similar commercial cultivar are provided below.

Plant description:

*Growth habit*.—Broad spreading to upright herbaceous perennial with foliage growth from basal shoots.

*Plant profile shape*.—Globular to flattened globular.

*Height*.—25 cm at approximately 12 months of age.

*Width*.—40 cm at approximately 12 months of age.

*Number of basal shoots per plant*.—1.

*Propagation*.—Type — Asexual propagation is accomplished by way of meristematic tissue culture micropropagation. Time to initiate roots — Approximately 4 to 6 weeks to initiate roots at an average ambient temperature of 21 degrees Celsius. Crop time — Approximately 16 to 20 weeks to produce a well-rooted, marketable 17 cm container from a rooted cutting.

*Disease and pest resistance or susceptibility*.—Neither susceptibility nor resistance to pests and diseases common to either *Philodendron* have been observed.

*Environmental tolerances*.—Adapt to temperatures as low as 5 degrees Celsius and at least as high as 40 degrees Celsius; moderate to high tolerance to rain; low to moderate tolerance to wind.

Roots:

*Density*.—Not very dense.

*Texture*.—Fleshy, non-fibrous.

*Color*.—Greyed-orange, RHS 161C.

Foliage:

*Quantity*.—7 leaves per shoot.

*Arrangement*.—Alternate whorl.

*Attachment*.—Petiolate.

*Division*.—Simple.

*Lamina*.—Shape — Ovate to near-cordate. Length — 9.0 cm, excluding the petiole. Width — 5.3 cm. Apex — Acuminate. Base — Rounded to cordate; basal lobes are free. Aspect — Flat to slightly concave. Margins — Entire; no undulation to very slightly undulated. Texture and luster, adaxial surface — Smooth, glabrous and glossy. Texture and luster, abaxial surface — Smooth, glabrous and glossy. Juvenile and mature color, adaxial and abaxial surfaces — Variegated foliage comprised of a mixture of light green, mid-green, and dark green base color, light yellow to golden yellow flecking, and irregular blotches of varying size and color, from near-white to golden yellow. In many instances the blotches cover one half or nearly one half of the lamina, from the main vein to the margin; in other instances, the blotches occur near the base of the lamina, and, in other instances, the blotches occur in the marginal zone. In some instances, laminas are predominantly green with yellow flecking, and nearly devoid of any blotches. The variegation pattern is variable from one leaf to the next. However, regardless of the variegation pattern and the amount of each color present, the color recitations are the same in both juvenile and mature foliage, adaxial and abaxial surfaces. The light green coloration is yellow-green, nearest to a blend of RHS 144D and 145B; the mid-green coloration is nearest to a blend of RHS 138B and 139C; the dark green coloration is nearest to a blend of RHS 139A and 141A; the light yellow coloration is nearest to a combination of RHS 10C and 11D; the golden yellow coloration is nearest to yellow-green, RHS 151B; the near-white coloration is RHS 155B, and these blotches may or may not be suffused with yellow-white, RHS 158D, or yellow, RHS 11D. Additionally, epidermal blistering may also be present on the green portions of the lamina, which creates the appearance of greyed-green blotches, nearest to RHS 192A. Venation — Pattern — Arcuate. Color, adaxial surfaces — The main vein and lateral veins are largely indistinguishable from the surrounding foliage; where veins are visible, the color is greyed-green nearest to RHS 191A. Color, abaxial surface — The main vein and lateral veins are largely indistinguishable from the surrounding foliage; where veins are visible on the light yellow, yellow, or near-white portions of the lamina, the vein color is greyed-yellow, nearest to in between RHS 161D and 162D; where veins are visible on the green portions of the lamina, the vein colors is green, RHS 134A.

*Petiole*.—Attitude — Upright and outward. Strength — Moderately strong. Aspect — Subterete. Length — 6.0 cm. Width — 0.8 cm, at the base, excluding the petiole wings. Texture and luster, adaxial surface — Smooth, glabrous and glossy. Texture and luster, abaxial surface — Smooth, glabrous and glossy. Juvenile and mature color, adaxial and abaxial surfaces — Green, nearest to a blend of RHS 138B and 139C, with irregular longitudinal striping in colors ranging from near-white, RHS 155B, with yellow-white suffusion, RHS 158C, to yellow, RHS 11D. Petiole Wings — Position —

Proximal end of the petiole. Length — 2.0 cm. Width — 0.6 cm. Color, adaxial and abaxial surfaces — Yellow-green, RHS 144D, and irregularly striped with colors ranging from near-white, RHS 155B, with yellow-white suffusion, RHS 158C, to yellow, RHS 11D. The base of the wings fade to near-white, RHS 155A.

Inflorescence: No flowering has been observed to date.

Flower buds: No flowering has been observed to date.

Flowers: No flowering has been observed to date.

Reproductive organs: No flowering has been observed to date.

Seed and fruit: No flowering has been observed to date.

COMPARISONS WITH THE PARENT PLANT AND CLOSEST KNOWN COMMERCIAL COMPARATOR

Plants of the new cultivar 'HUTAPD75' differ from the seed parent, *Philodendron* 'White Wizard' (not patented), by the characteristics described in Table 1 below.

TABLE 1

Comparison Between 'HUTAPD75' and The Parent

| Characteristic | 'HUTAPD75' | 'White Wizard' |
|---|---|---|
| General coloration of the petiole. | Green with a combination of both near-white and light-yellow irregular longitudinal striping. | Green with white striping. |
| General coloration of the mature adaxial foliar surface. | Variegated foliage comprised of a green base coloration, light yellow to golden yellow flecking, and irregular blotches of varying size and color, from near-white to yellow. | Variegated foliage comprised of a green general base coloration, with near-white flecking and blotching. |

COMPARISONS WITH THE MOST SIMILAR COMMERCIAL VARIETY

Plants of the new cultivar 'HUTAHM05' may be distinguished from the most similar commercial comparator known to the inventor, *Philodendron erubescens* 'Princess Taffy' (U.S. Plant Pat. No. 36,203), by the characteristics described in Table 2.

TABLE 2

Comparison Between 'HUTAPD75' and 'Princess Taffy'

| Characteristic | 'HUTAPD75' | 'Princess Taffy' |
|---|---|---|
| Length to width ratio of the lamina. | 1.7:1 to 1.85:1. | 2.0:1 to 3.0:1. |
| General coloration of the petiole. | Green with a combination of both near-white and light-yellow irregular longitudinal striping. | Green with a combination of both light red-purple, green-yellow, and light-yellow irregular longitudinal striping. |

That which is claimed is:

1. A new and distinct variety of *Philodendron* plant named 'HUTAPD75', substantially as described and illustrated herein.

* * * * *